US011243204B2

(12) United States Patent
Castrop

(10) Patent No.: US 11,243,204 B2
(45) Date of Patent: *Feb. 8, 2022

(54) METHOD FOR DETECTING THE PRESENCE OF MYCOBACTERIAL MATERIAL IN A SAMPLE USING AT LEAST TWO ANTIGENS

(71) Applicants: KEI INTERNATIONAL LIMITED, North Point (HK); TOMORROWS IP LIMITED, North Point (HK)

(72) Inventor: Johannes Theodorus Castrop, Woudenberg (NL)

(73) Assignees: KEI INTERNATIONAL LIMITED; TOMORROWS IP LIMITED

( * ) Notice: Subject to any disclaimer, the term of this patent is extended or adjusted under 35 U.S.C. 154(b) by 0 days.

This patent is subject to a terminal disclaimer.

(21) Appl. No.: 16/307,422

(22) PCT Filed: Jun. 8, 2017

(86) PCT No.: PCT/CN2017/087547
§ 371 (c)(1),
(2) Date: Dec. 5, 2018

(87) PCT Pub. No.: WO2017/211316
PCT Pub. Date: Dec. 14, 2017

(65) Prior Publication Data
US 2019/0219574 A1    Jul. 18, 2019

(30) Foreign Application Priority Data

Jun. 8, 2016  (NL) .................................. NL2016913
Jun. 8, 2016  (NL) .................................. NL2016914
Jul. 21, 2016  (NL) .................................. NL2017204

(51) Int. Cl.
*G01N 33/569* (2006.01)
*C07H 11/04* (2006.01)

(52) U.S. Cl.
CPC ......... *G01N 33/5695* (2013.01); *C07H 11/04* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 5,597,735 A | 1/1997 | Laszlo et al. ................. | 436/525 |
| 5,721,109 A | 2/1998 | Yano et al. .................. | 435/7.32 |
| 6,416,962 B1 | 7/2002 | Das et al. .................... | 435/7.32 |
| 7,851,166 B2 | 12/2010 | Verschoor et al. ............ | 435/7.2 |
| 8,030,088 B2 | 10/2011 | McCash et al. .............. | 436/164 |
| 10,921,322 B2 | 2/2021 | Castrop ........... G01N 33/56933 | |
| 2003/0143652 A1 | 7/2003 | Simonson ..................... | 435/7.32 |
| 2004/0132106 A1 | 7/2004 | Houthoff et al. ............. | 435/7.1 |
| 2007/0243557 A1 | 10/2007 | Friedman et al. ............ | 435/7.1 |
| 2008/0064051 A1 | 3/2008 | Hasnain et al. ............. | 435/7.92 |
| 2009/0111125 A1 | 4/2009 | Verschoor ..................... | 435/7.21 |
| 2011/0280930 A1 | 11/2011 | Batista et al. ................. | 424/450 |
| 2012/0301510 A1 | 11/2012 | Kishimoto et al. ........... | 424/400 |
| 2019/0219574 A1 | 7/2019 | Castrop .............. | G01N 33/5695 |

FOREIGN PATENT DOCUMENTS

| | | | | |
|---|---|---|---|---|
| CN | 102707053 | | 10/2012 | .......... G01N 33/543 |
| CN | 102818889 | | 12/2012 | .......... G01N 33/545 |
| EP | 0921397 | | 6/1999 | .......... G01N 33/569 |
| EP | 1950218 | | 7/2008 | ............ C07H 13/06 |
| EP | 1950218 A1 | * | 7/2008 | ............ C07H 13/06 |
| EP | 2272860 | | 1/2011 | .......... G01N 33/543 |
| EP | 2416158 | | 2/2012 | .......... G01N 33/543 |
| NL | 2017204 | | 7/2016 | .......... G01N 33/569 |
| RU | 2470801 | | 6/2011 | ............... B60P 3/00 |
| WO | WO9414069 | | 6/1994 | .......... G01N 33/569 |
| WO | WO9424560 | | 10/1994 | .......... G01N 33/543 |
| WO | WO2004112694 | | 12/2004 | |
| WO | WO2005116654 | | 12/2005 | .......... G01N 33/569 |
| WO | WO2006026404 | | 3/2006 | |
| WO | WO2009133378 | | 11/2009 | .......... G01N 33/543 |
| WO | WO2010008667 | | 1/2010 | ............. A61L 27/54 |
| WO | WO2012119128 | | 3/2012 | ................ B01L 3/00 |
| WO | WO2012151039 | | 11/2012 | ......... A61K 31/6615 |
| WO | WO2013186679 | | 12/2013 | .......... G01N 33/543 |

(Continued)

OTHER PUBLICATIONS

Laszio et al. 1992 (Comparison of Bis-di-octadecylamide of trehalose Dicarboxylic Acid (BDA.TDA) with glycolipid SL-IV as ELISA antigens for the serodiagnosis of Leprosy; International Journal of Leprosy; 60(3):376-381). (Year: 1992).*

Julian et al. 2004 (Comparison of Antibody Responses to a Potential Combination of Specific Glycolipids and Proteins for Test Sensitivity Improvement in Tuberculosis Serodiagnosis; Clinical and Diagnostic Laboratory Immunology 11(1): 70-76). (Year: 2004).*

Julian et al. 2001 (An ELISA for five glycolipids from the cell wall of *Mycobacterium tuberculosis*: Tween 20 interference in the assay; Journal of Immunological Methods 251: 21-30) (Year: 2001).*

Angala et al., The cell envelope glycoconjugates of *Mycobacterium tuberculosis*, Critical Reviews in Biochemistry and Molecular Biology, 2017 (40 pgs).

Astarie-Dequeker et al., The role of mycobacterial lipids in host pathogenesis, Drug Discover Today: Disease Mechanisms,, vol. 7, No. 1, 2010 (9 pgs).

(Continued)

*Primary Examiner* — Mary Maille Lyons
(74) *Attorney, Agent, or Firm* — Hayes Soloway P.C.

(57) ABSTRACT

Disclosed is a method of detecting the presence of antibodies against mycobacterial material in a sample by detecting binding of antibodies in said sample to at least two types of immobilised antigen, which antigens are capable of binding to an antibody which is indicative for the presence of mycobacterial material in a human or animal. Also disclosed is a solid substrate including a combination of said at least two antigens immobilised to said substrate, and to a biosensor having at least two types of immobilised antigen, which antigens are capable of binding to an antibody which is indicative for the presence of mycobacterial material in a human or animal.

7 Claims, 4 Drawing Sheets

(56) References Cited

FOREIGN PATENT DOCUMENTS

| WO | WO2014184768 | | 11/2014 | ........... G01N 33/569 |
|---|---|---|---|---|
| WO | WO2014210327 | | 12/2014 | ............ A61K 31/06 |
| WO | WO-2014210327 A1 | * | 12/2014 | ......... G01N 33/5695 |
| WO | WO2016024116 | | 2/2016 | ........... G01N 33/543 |
| WO | WO-2016024116 A1 | * | 2/2016 | ........... G01N 33/543 |
| WO | WO2017211314 | | 12/2017 | ........... G01N 33/543 |
| WO | WO2017211316 | | 12/2017 | ........... G01N 33/569 |

OTHER PUBLICATIONS

Buter et al., Stereoselective Synthesis of 1-Tuberculosinyl Adenosine; a Virulence Factor of *Mycobacterium tuberculosis*, J Org Chem, 2016, 81(15) (25 pgs).
Di Libero et al., Recognition of Lipid Antigens by T Cells, Nature Reviews/Immunology, vol. 5, 2005 (12 pgs).
Garżon et al., Predicted structural basis for CD1c presentation of mycobacterial branched polyketides and long lipopeptide antigens, Molecular Immunology 47 (2009) 253-260 (8 pgs).
Geerdink et al., Total synthesis, stereochemical elucidation and biological evaluation of Ac$_2$SGL; a 1,3-methyl branched sulfoglycolipid from *Mycobacterium tuberculosis*, Chemical Science, No. 2, 2013, abstract only (3 pgs).
Gilleron et al., Diacylated Sulfoglycolipids Are Novel Mycobacterial Antigens Stimulating CD1-restricted T Cells during Infection with *Mycobacterium tuberculosis*, The Journal of Experimental Medicine, 2004 (11 pgs).
International Preliminary Report on Patentability issued in application No. PCT/CN2017/087547, dated Dec. 11, 2018 (8 pgs).
International Search Report and Written Opinion issued in application No. PCT/CN2017/087547, dated Aug. 28, 2017 (13 pgs).
Layre et al., Molecular profiling of *Mycobacterium tuberculosis* identifies tuberculosinyl nucleoside products of the virulence-associated enzyme Rv3378c, PNAS, 2014, vol. 11, No. 8, 2978-2983 (6 pgs).
Li et al., Highly Stereocontrolled Total Synthesis of β-D-Mannosyl Phosphomycoketide: A Natural Product from *Mycobacterium tuberculosis*, The Journal of Organic Chemistry, 2013, 78, 5970-5986 (17 pgs).
Matsunaga et al., Mycoketide: A CD1c-Presented Antigen with Important Implications in Mycobacterial Infection, Clinical and Developmental Immunology, 2012 (8 pgs).
Tiwari et al., Glygolipids of *Mycobacterium tuberculosis* Strain H37Rv Are Potential Serological markers for Diagnosis of Active Tuberculosis, Clinical and Diagnostic Laboratory Immunology, 2005, 465-43 (9 pgs).
Van Summeren et al., Total Synthesis of Enantiopure β-D-Mannosyl Phosphomycoketides from *Mycobacterium tuberculosis*, J. Am. Chem. Soc., 2006, 128, 4546-4547 (2 pgs).
Young et al., In Vivo Biosynthesis of Terpene Nucleosides Provides Unique Chemical Markers of *Mycobacterium tuberculosis* Infection, Chemistry & Biology 22, 2015, 516-526 (12 pgs).
European Search Report for Application Serial No. 17 80 9753, dated Oct. 4, 2019 (5 pages).
De Jong et al., "CD1c Presentation of Synthetic Glycolipid Antigens with Foreign Alkyl Branching Motifs," Chemistry & Biology 14, 1232-1242, Nov. 2007 (11 pgs).
De Libero et al., "Recognition of Lipid Antigens by T Cells," Nature Reviews/Immunology, vol. 5, Jun. 2005 (12 pgs).
International Search Report and Written Opinion issued in application No. PCT/CN2017/087542, dated Aug. 18, 2017 (11 pgs).
Moody et al., "CD1c-mediated T-cell recognition of isoprenoid glycolipids in *Mycobacterium tuberculosis* infection," Nature, vol. 404, Apr. 20, 2000 (5 pgs).
Camacho et al., "Phage display of functional αβ single-chain T-cell receptor molecules specific for CD1b:Ac$_2$SGL complexes from *Mycobacterium tuberculosis*-infected cells", Bio Med Central, BMC Immunology 2013, 14 (Suppl 1): 52 (4 pages).

Dang et al., "Direct detection of *Mycobacterium tuberculosis* in sputum using combined solid phase extraction-gas chromatography-mass spectrometry", Journal of Chromatography B, pp. 986-987 (2015) 115-122 (8 pages).
Egorov, "Physicochemical Patterns of Antigen-Antibody Interactions", Chapter 2, pp. 33-35 with English Translation (4 pages).
Julian et al. 2001 (An ELISA for five glycolipids from the cell wall of *Mycobacterium W tuberculosis*: Tween 20 interference in the assay; Journal of Immunological Methods 251: 21-30) (Year: 2001).
Kim et al., "Diagnosis of Tuberculosis Using a Liquid Crystal-Based Optical Sensor", Macromolecular Research, The Polymer Society of Korea and Springer, Nov. 2015 (8 pages).
Hermanson, "Chapter 3—The Reactions of Bioconjugation," in Bioconjugate Techniques, Third Edition, Academic Press, 2013, pp. 229-258 (30 pages).
Office Action issued in U.S. Appl. No. 16/307,427, dated Mar. 10, 2021, 56 pages.
Boulous et al. Journal of Publich Health Infomatics 5(3) 2014.
Chamanzar et al., "Hybrid photonic surface-plasmon-polariton ring resonators for sensing applications," Applied Physics B, vol. 101, No. 1-2, Oct. 2010, pp. 263-271 (9 pgs).
Cruaud et al., "Human IgG Antibodies Immunoreacting with Specific Sulfolipids from *Mycobacterium tuberculosis*", Zbl. Bakt. 271, 481-485 (1989) (5 pgs).
Hamilton et al., "Naturally occurring carbohydrate antibodies: Interference in solid-phase imunoassays" *Journal of Immunological Methods*, vol. 77, Issue 1, Feb. 28, 1985, pp. 95-108, Abstract only (2 pgs).
Huebner, Johannes, "Antibody-Antigen Interaction and Measurements of Immunologic Reactions", Chapter 9, 2004(26 pages).
International Preliminary Report on Patentability issued in application No. PCT/NL2016/050002, dated Dec. 19, 2016 (30 pgs).
International Preliminary Report on Patentability issued in application No. PCT/CN2019/099736, dated Feb. 9, 2021 (7 pgs).
International Preliminary Report on Patentability issued in application No. PCT/CN2019/124224, dated Mar. 19, 2021 (4 pgs).
International Search Report and Written Opinion issued in application No. PCT/CN2019/124224, dated Mar. 6, 2020 (11 pgs).
International Search Report and Written Opinion issued in application No. PCT/NL2016/050002, dated Jun. 30, 2016 (13 pgs)
International Search Report and Written Opinion issued in application No. PCT/CN2019/099736, dated Nov. 6, 2019 (11 pgs).
International Search Report and Written Opinion issued in application No. NL2022166, dated Dec. 10, 2018 (11 pgs).
International Search Report and Written Opinion issued in application No. NL2021443, dated Mar. 27, 2019 (11 pgs).
Jain et al. 2017 "The principals and applications of avidin-based nanoparticles in drug delivery and diagnosis", J. Control Release Jan. 10, 2017; 245: 27-40 (36 pgs).
Julian et al. 2002 (Serodiagnosis of Tuberculosis: Comparison of Immunoglobulin A (IgA) Response to Sulfolipid I with IgG and IgM Responses to 2,3-Diacyltrehalose, 2,3,6-Triacyltrehalose, and Cord Factor Antigens, Journal of Clinical Microbiology, Oct. 2002, pp. 3782-3788 (7 pages).
Law, B., "Immunoassay: a practical guide," Taylor & Francis e-Library, 2005 (15 pgs).
Lemmer et al., "Detection of Antimycolic Acid Antibodies by Liposomal Biosensors," Methods in Enzymology, No. 464, Jan. 2009, pp. 79-104 (26 pgs).
Mathebula et al., "Recognition of anti-mycolic acid antibody at self-assembled mycolic acid antigens on a gold electrode: a potential impedimetric immunosensing platform for active tuberculosis," Chemical Communications, No. 23, May 2009, pp. 3345-3347 (3 pgs).
Pavlickova P., Hug H. (2004) A Streptavidin-Biotin-Based Microarray Platform for Immunoassays. In: Fung E.T. (eds) Protein Arrays. Methods in Molecular Biology, vol. 264. Humana Press. https://doi.org/10.1385/1-59259-759-9:073 (Abstract and Fig 2 only).
Thanyani et al., "A novel application of affinity biosensor technology to detect antibodies to mycolic acid in tuberculosis patients," Journal of Immunological Methods, vol. 332, Jan. 2008, pp. 61-72 (12 pgs).

(56) References Cited

OTHER PUBLICATIONS

Thanyani, S.T., "An assessment of two evanescent field biosensors in the development of an immunoassay for tuberculosis," partial fulfillment of the requirements for the PhD Degree in Biochemistry in the Faculty of Natural & Agricultural Sciences, University of Pretoria, Jul. 2008 (194 pgs).

* cited by examiner

METHOD FOR DETECTING THE PRESENCE OF MYCOBACTERIAL MATERIAL IN A SAMPLE USING AT LEAST TWO ANTIGENS

The present invention relates to a method of detecting the presence of antibodies against mycobacterial material in a sample detecting binding of antibodies in said sample to at least two types of immobilised antigen, which antigens are capable of binding to an antibody which is indicative for the presence of mycobacterial material in a human or animal. The invention also relates to a solid substrate comprising a combination of said at least two antigens immobilised to said substrate, and the invention also relates to a biosensor comprising at least two types of immobilised antigen, which antigens are capable of binding to an antibody which is indicative for the presence of mycobacterial material in a human or animal.

INTRODUCTION

*Mycobacterium tuberculosis* is a pathogenic bacterial species in the family Mycobacteriaceae and the causative agent of most cases of tuberculosis (TB).

TB is still one of the leading causes of death in many low and middle income countries. In addition, more and more cases are reported of multi-drug resistant TB.

A reliable and fast way of diagnosing tuberculosis is therefore of utmost importance.

Several methods of diagnosing tuberculosis have been developed, but all methods have their disadvantages.

Diagnosing tuberculosis based merely on signs and symptoms is difficult, as is diagnosing the disease in those who are immunosuppressed. The TB skin test (also called the Mantoux tuberculin skin test), TB blood tests (also called interferon-gamma release assays or IGRAs), and chest radiography (X-ray), and tests on the presence of acid-fast-bacilli (AFB) on a sputum smear, indicate some of the infected individuals in days.

Sputum smear microscopy (also referred to as smear test) is a common method for diagnosis of pulmonary tuberculosis in low and middle income countries where most TB cases occur. Although it is a simple, rapid and inexpensive technique which is used in areas with a very high prevalence of tuberculosis, there are significant limitations in its performance. For instance, the sensitivity is severely compromised when the bacterial load is less than 10,000 *Mycobacterium tuberculosis* organisms/ml sputum sample. A person that tests positive in a smear test (smear positive person) thus has a very high bacterial load and will thus be in a very advanced stage of TB. In smear positive persons it is usually clear at first sight that the person suffers from an illness. In such advanced stages, often no successful treatment is possible anymore. On the other hand, no conclusion can be drawn if a person tests negative in a smear test (smear negative person), because that person could suffer from TB in a less advanced stage, which is associated with a lower bacterial load. In smear negative persons it is usually not clear at first sight that the person suffers from an illness. In addition, the smear test also gives poor results in extra-pulmonary tuberculosis, pediatric tuberculosis and in patients co-infected with HIV and tuberculosis.

Humans or animals infected with *M. tuberculosis* normally produce antibodies directed against the *Mycobacterium*. The presence of these antibodies in a sample taken from infected individuals indicates the infection. The most common *Mycobacterium* specific antigens are mycolic acids or derivatives thereof. For instance, WO 2005/116654 and WO 2013/186679 describe methods of antibodies in a sample against mycolic acids for the diagnosis of active tuberculosis, by detecting binding of antibodies to immobilised mycolic acid antigens.

The inventor has observed in samples derived from healthy subjects a high degree of binding of materials contained in these samples to immobilised mycolic acid antigens when used as sole type of antigens, which indicates that samples derived from healthy subjects contain materials which bind to mycolic acid antigens, but which are not indicative for tuberculosis. This may lead to a false positive outcome. Thus, in case a subject actually suffers from tuberculosis, the problem arises that if materials that are not indicative for tuberculosis bind to immobilised mycolic acid antigens in a detection test, a high background binding signal is produced. This high background signal may obscure the signal derived from the actual markers for tuberculosis. So, there is also the risk of false negative results. The inventor therefore considers that there is room for improvement with respect to the sensitivity of detection of tuberculosis.

The present invention therefore aims to overcome the problems that derive from the binding of materials that are not indicative for tuberculosis to immobilised mycolic acid antigens and to improve the sensitivity and reliability of detection of tuberculosis.

SUMMARY OF THE INVENTION

The aim of the invention has been achieved by the provision of a method of detecting the presence of antibodies against mycobacterial material in a sample comprising the steps of: providing a sample from a human or animal; and detecting binding of antibodies in said sample to at least two types of immobilised antigens capable of binding to an antibody which is indicative for the presence of mycobacterial material in a human or animal, selected from the following group:

A) a mycolic acid derived antigen, optionally modified with one or more functional groups that enable immobilisation to a solid substrate, B) a diacyl glycolipid antigen; represented by the following formula (I)

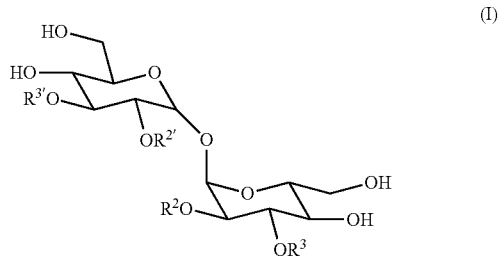

wherein:
$R^2$ and $R^3$, identical or different, are independently chosen from H, $SO_3H$, $SO_3^-$ or $SO_3^-/M^+$, wherein $M^+$ is a cation; and $R^{2'}$ and $R^{3'}$, identical or different, are acyl groups, wherein the antigen represented by formula (I) is optionally modified with one or more functional groups that enable immobilisation to a solid substrate, and enantiomers, diastereoisomers, and mixtures thereof; and C) a tuberculosinyl adenosine antigen; represented by the following formula (II):

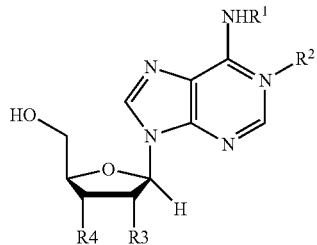
(II)

wherein in formula (I) $R^1$ is H or a group with formula (III)

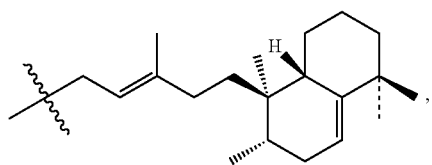
(III)

$R^2$ is absent or a group with formula (III), provided that one of $R^1$ and $R^2$ is a group with formula (III), $R^3$ and $R^4$ are selected independently from hydrogen, OH, a carboxylic acid group or an acyl group, in any combination thereof, wherein said tuberculosinyl adenosine antigen is optionally modified with one or more functional groups that enable immobilisation to a solid substrate, and enantiomers, diastereoisomers of the antigens, and mixtures thereof.

In a second aspect the invention relates to a solid substrate, comprising a combination of 2 or more of the types of tuberculosinyl adenosine antigens, diacyl glycolipid antigens, and mycolic acid derived antigens as defined above in relation to the first aspect of the invention, immobilised to said substrate.

In a third aspect the invention relates to a biosensor, comprising a combination of 2 or more of the tuberculosinyl adenosine antigens, diacyl glycolipid antigens, and mycolic acid derived antigens as defined above in relation to the first aspect of the invention.

SHORT DESCRIPTION OF THE FIGURES

DETAILED DESCRIPTION

Figure 1:
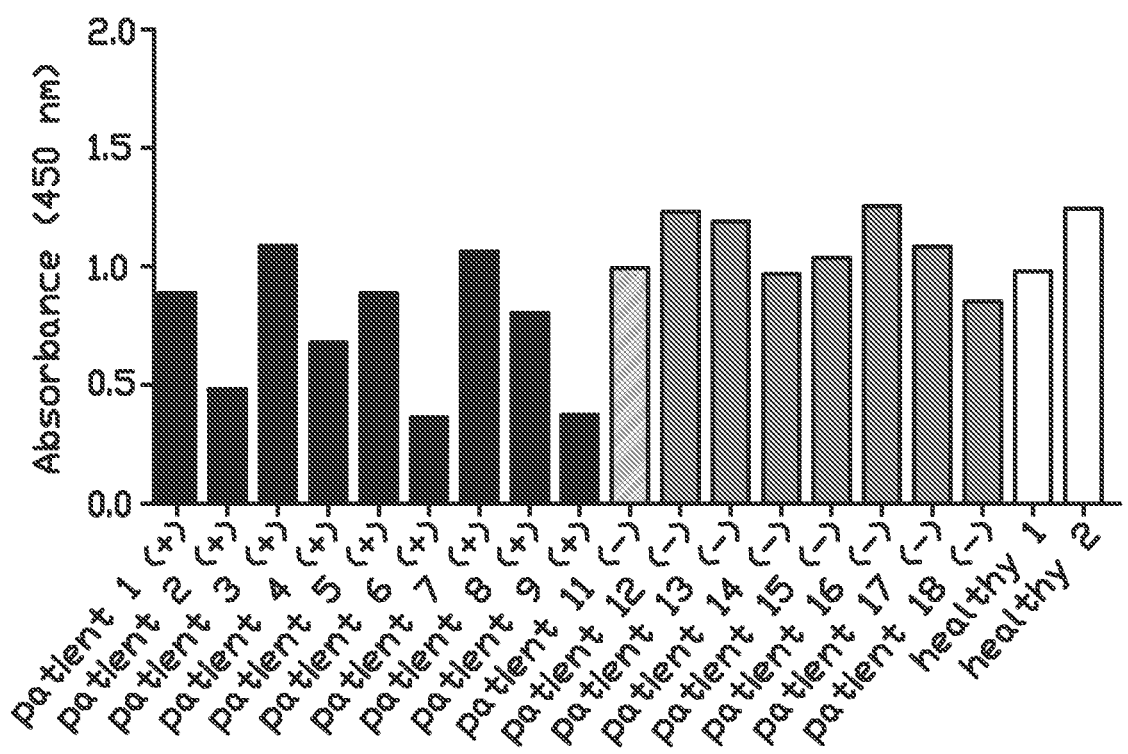
FIG. 1 shows a diagram with ELISA results using mycolic acid immobilised on ELISA plates (IgM as secondary antibody).

The present invention is based on the observation that exposing a sample from a human or animal to at least two types of immobilised antigens capable of binding to an antibody which is indicative for the presence of mycobacterial material in a human or animal and selected from the following group:
A) a mycolic acid derived antigen,
B) a diacyl glycolipid antigen; and
C) a tuberculosinyl adenosine antigen; as defined above, and detecting binding of antibodies in said sample to said antigens, leads to improved reliability and sensitivity of a tuberculosis test.

The mycolic acid derived antigens as referred to in the present application may be derived from mycobacteria selected from virulent and pathogenic mycobacteria. The term mycolic acid derived antigen is to be understood as a compound comprising a mycolic acid residue which is capable of binding to anti-mycolic acid antibodies. Preferably, the mycolic acid antigen is derived from *Mycobacterium tuberculosis*. Said mycolic acid derived antigen may be at least one selected from the group of mycolic acid, cord factor, chemically modified mycolic acid, chemically modified cord factor, a synthetic mycolic acid derivative, a synthetic cord factor derivative.

The mycolic acid derived antigen may suitably be selected from one or more of mycolic acids obtained from natural sources, synthetically prepared mycolic acids, sulfur-containing mycolic acids, structural analogues of mycolic acids, and mycolic acid wax esters. The mycolic acid derived antigen also includes salts and/or esters of these derivatives.

Natural sources of mycolic acid derivatives include the cell walls of mycobacteria such as *Mycobacterium tuberculosis* include mixtures of different classes of compounds and different mycolic acid homologues, often as derivatives in which they are bonded to the wall of the cell.

It may be preferred to use synthetically prepared mycolic acids because then it can be exactly determined which and which amount of a particular derivative is used. This is advantageous for obtaining a high substrate selectivity.

Therefore in order to be able to provide a detection with high reliability and reproducible results it is preferred to use semi-synthetic or even more preferred synthetic mycolic acid derivatives which are identical or closely analogous to single compounds found in natural mixtures.

Esters of mycolic acid derivatives can also be used such as esters of alcohols (e.g. monohydric alcohols and polyhydric alcohols) and sugar esters. Sugar esters are particularly preferred. Sugar esters include esters with a monosaccharide, disaccharide or an oligosaccharide. Said saccharides may conveniently include sugar units based on hexoses and/or pentoses. Glucose esters are suitable examples of these esters. Further suitable sugar esters are trehalose esters, including trehalose monomycolates and trehalose dimycolates. For instance cord factors, which are trehalose monomycolates or trehalose dimycolates are well known examples of sugar esters that are suitable. These compounds occur in nature as complex mixtures of different classes of mycolic acids and of different homologues within each class.

Because it is difficult to establish the identity of cord factors present in natural products and to separate individual molecular species it is preferred to use semi-synthetic or more preferably synthetic mycolic acid derivatives for the purposes of the invention. Further, it is known that the structure of the mycolic acid unit affects the biological activity of the cord factor. Suitable semi-synthetic derivatives include semi-synthetic cord-factors which may be prepared by attaching mycolic acids to the sugar group. These semi-synthetic factors however still contain mixtures of different homologue. Therefore particular suitable mycolic acid derivatives for use in the context of the present invention are synthetic cord factors, for example the synthetic cord factors described in WO 2010/08667, i.e. compounds of formula $(M)_x (S)_y (M')_z$, wherein x is from 1 to 6, y is from 1 to 12, z is from 0 to 10, each M and each M' is independently a mycolic acid residue including a β-hydroxy acid moiety and each S is a monosaccharide unit.

Salts of mycolic acid derivatives can also be used, for instance ammonium salts, or alkali metal and alkaline earth metal salts.

Sulfur-containing mycolic acids and/or esters or salts thereof may also be used. These compounds are analogues of natural mycolic acid compounds containing sulfur.

Mycolic acid wax esters comprise a cyclopropyl group or an alkene and an internal ester group and can be isolated from natural sources or prepared synthetically.

Suitable compounds for use in the detection method of the invention are described inter alia in WO 2016/024116.

The mycolic acid antigen may be in a form selected from homogenous and heterogenous compound mixtures. The mycolic acid derived antigen may for instance be used in combination with a phospholipid such as phosphatidylcholine.

Although the use of mycolic acid involves a risk of false positive/negative signal, detection of binding of antibodies in the sample to mycolic acid derived antigens in combination with one or two of the other types of antigens as defined above provides an additional indication of whether or not a person is infected with tuberculosis or not. This further enhances the reliability of the method of the invention.

The term "diacyl glycolipid antigens" in this application is meant to refer to diacylated trehalose structures as defined in the following structures (I) and (IV) to (XIII).

The inventor has surprisingly found that if these immobilised diacyl glycolipid antigens are used in as one of the at least two types of antigens in accordance with the invention, a very high tuberculosis specific binding of antibodies to these antigens is detected. The signal derived from the actual markers for tuberculosis is significantly less obscured by a background signal than when immobilised mycolic antigens are used, so that the signal derived from the actual markers for tuberculosis becomes more pronounced. This way the invention provides a significant improvement with regard to the sensitivity of detection of markers for tuberculosis.

Further in this respect it is noted that when said immobilised diacyl glycolipid antigens in accordance with the invention are used in a method for detecting a marker for tuberculosis a very high tuberculosis specific binding of antibodies to these antigens is detected in particular in case of samples derived from patients that were tested smear negative. This makes it possible to diagnose TB in an early stage, in which there is a higher chance for successful treatment than in a later stage. The use of diacyl glycolipid antigens on the solid substrate of the invention makes it possible to detect low amounts of antibodies against mycobacterial material in a sample.

The immobilised diacyl glycolipid antigens of the invention perform very well when applied to samples derived from patients co-infected with HIV and tuberculosis.

These diacyl glycolipids, which are in fact diacylated trehalose antigens and therefore can also be referred to as diacylated trehalose antigens, or derivatives thereof can be defined as a compound represented by the following formula (I),

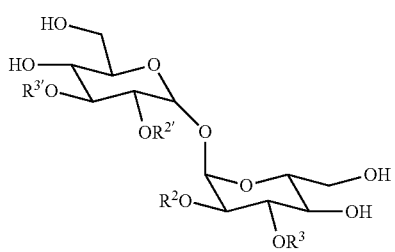

wherein: $R^2$ and $R^3$, identical or different, are independently chosen from H, $SO^3H$, $SO^{3-}$ or $SO^{3-}/M^+$ wherein $M^+$ is a cation, preferably a metal cation such as $Na^+$ or $K^+$; $R^{2'}$ and $R^{3'}$, identical or different, are acyl groups, wherein the antigen is optionally modified with one or more functional groups that enable immobilisation to a solid substrate. The diacyl glycolipids as described herein also include enantiomers, diastereoisomers, and mixtures the compounds of formula (I).

In formula (I) $R^{2'}$ and $R^{3'}$, identical or different, may be

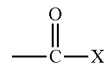

wherein X is independently chosen from an unsaturated or saturated linear or branched hydrocarbon chain, suitably an alkyl group, optionally substituted with one or more substituents and/or modified with one or more functional groups.

In a preferred embodiment of formula (I) $R^2$ is $SO^{3-}$, $SO^3H$ or $SO^{3-}/M^+$, wherein $M^+$ is a cation and $R^3$ is H. It is preferred that in case $R^2$ is $SO^{3-}/M^+$ that the cation is $Na^+$ or $K^+$.

In another preferred embodiment of formula (I) $R^2$ and $R^3$ are H.

It is preferred that in one of $R^{2'}$ and $R^{3'}$ of formula (I) X is a saturated linear hydrocarbon chain optionally substituted with one or more substituents and/or modified with one or more functional groups and wherein in the other of $R^{2'}$ and $R^{3'}$ X is a saturated branched hydrocarbon chain optionally substituted with one or more substituents and/or modified with one or more functional groups. In this respect it is further preferred that in formula (I) one of $R^{2'}$ and $R^{3'}$ is a group represented by the following formula (IV):

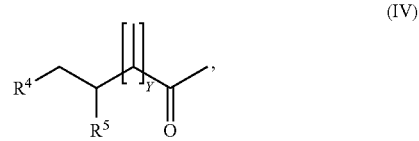

wherein $R^4$ is a linear saturated hydrocarbon chain with formula $C_nH_{n+1}$, wherein n is an integer between 1 and 20, optionally modified with one or more functional groups, and wherein Y is an integer between 1 and 10, and wherein $R^5$ is H or OH, and the other one of $R^{2'}$ and $R^{3'}$ is a linear saturated hydrocarbon chain with formula $C_nH_{n+1}$, wherein n is an integer between 1 and 20, optionally modified with one or more functional groups. It is preferred that the acyl chains represented by $R^{2'}$ and $R^{3'}$ are relatively short. This makes the antigens more soluble in aqueous solutions and thus easier in use. The increased hydrophilicity that results from relatively short acyl chains makes the detection surface or sensor surface to which the antigens are immobilised more hydrophilic. Because of this, interactions of antibodies in the antigen occur easier and the speed of the detection will be enhanced. Moreover, it will be easier to synthesize the antigens in case synthetic antigens are used. In this respect in antigens according to formula (I) with short $R^{2'}$ and $R^{3'}$ acyl chains $R^4$ may be a linear saturated hydrocarbon chain with formula $C_nH_{n+1}$, wherein n is an integer between 1 and 10, such as between 1 and 9, such as between 1 and 8, such as between 1 and 7, such as between 1 and 6 such as between 1 and 5 such as between 1 and 4 such as between 1 and 3, such as 1, 2, 3, 4, 5, 6, 7, 8 or 9, optionally modified with one or more functional groups, and wherein Y is an integer between 1 and 10, such as between 1 and 5, such as between 1 and 4, such as between 1 and 3, such as 1, 2, 3, or 5, optionally modified with one or more functional groups. The other one of $R^{2'}$ and $R^{3'}$ in this respect may be a linear saturated hydrocarbon chain with formula $C_nH_{n+1}$, wherein n is an integer between 1 and 15, such as between 1 and 14, such as between 1 and 13, such as between 1 and 12, such as between 1 and 11, such as between 1 and 10, such as between 1 and 9, such as between 1 and 8, such as between 1 and 7, such as between 1 and 6 such as between 1 and 5 such as between 1 and 4 such as between 1 and 3, such as between 1, 2, 3, 4, 5, 6, 7, 8, 9, 10, 11, 12, 13, 14 or 15 optionally modified with one or more functional groups. A suitable antigen in this respect would for example be compound (V):

(V)

wherein AcS represents a thio acetate group (and $M^+$ is a cation or absent). This exemplary molecule is modified with a thio acetate group to enable immobilisation to a solid substrate, for instance a silica substrate or gold substrate. An antigen with a thiol group can be directly immobilised to gold. For silica substrates the substrate suitably can be coated with a silane active group to which the thiol of the modified antigen can bind. In case the diacyl glycolipid antigen is present in *Mycobacterium, tuberculosis* it may be isolated from *Mycobacterium tuberculosis*. Alternatively, it may be synthesized, for instance by a method as adapted from what is described in EP 1 950 218 A1. If the antigen is not present in *Mycobacterium tuberculosis* it may be modified from an antigen isolated from *Mycobacterium tuberculosis* or synthesized.

It is highly preferred that the further antigen is a diacylated sulfoglycolipid ($Ac_2SGL$) as found in *Mycobacterium tuberculosis*, optionally modified with one or more functional groups. In a preferred embodiment said $Ac_2SGL$ is 2-palmitoyl-3-hydroxyphthioceranoyl-2'-sulfate-α-α'-D-trehalose or 2-stearoyl-3-hydroxyphthioceranoyl-2'-sulfate-α-α'-D-trehalose, optionally modified with one or more functional groups. $Ac_2SGL$ molecules feature a trehalose 2'-sulfate core, and are diacylated with either a palmitic or stearic residue at the 2-position and hydroxyphthioceranic acid, with varying length and methyl substituents, at the 3-position, for instance compound (VI):

(VI)

wherein $R^2$ is $SO_3^-$, $SO_3H$ or $SO_3^-/M^+$, wherein $M^+$ is a kation, preferably a metal cation, preferably $Na^+$ or $K^+$.
Further examples are represented by formulae VII, VIII and IX below.

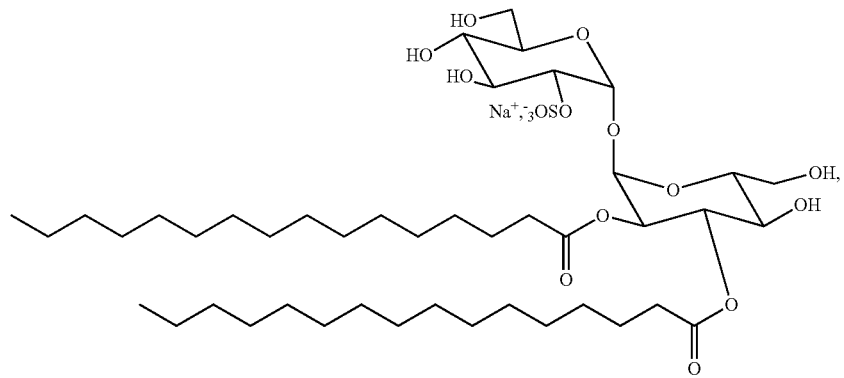
(VII)
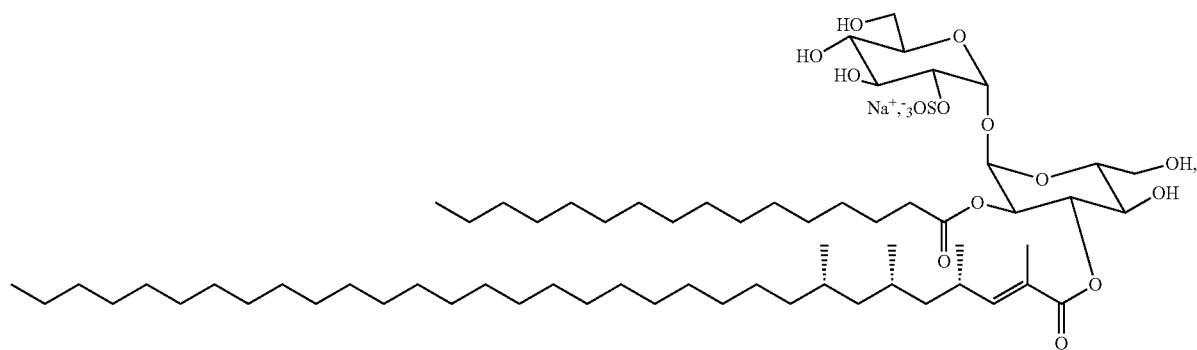
(VIII)
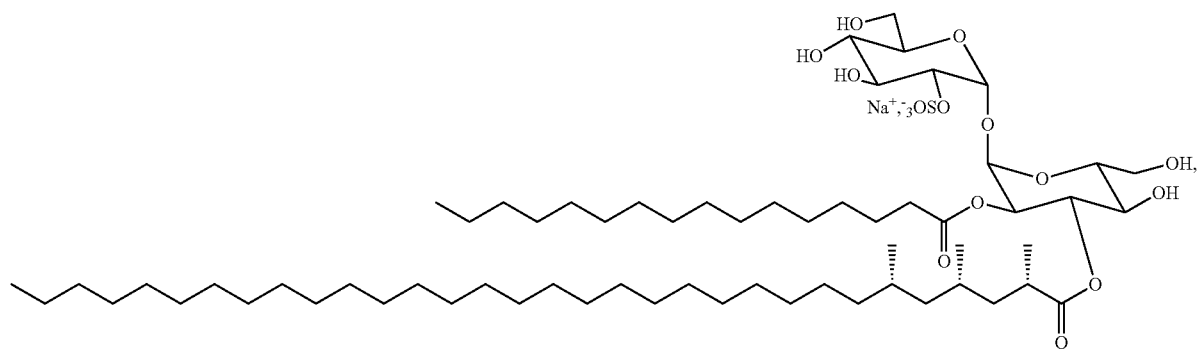
(IX)

wherein in formulae VII, VIII and IX the $SO_3^-/Na^+$ moiety may also be $SO_3^-$, $SO_3H$ and $Na+$ may also be another kation such as $K^+$.

In a further preferred embodiment the diacyl glycolipid antigens as defined above may be represented by formula (X):

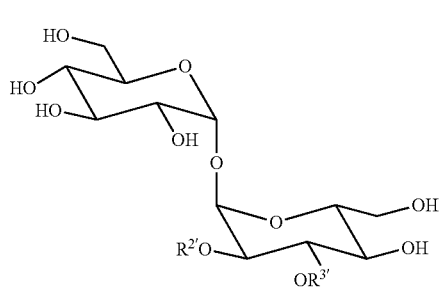

R2' and R3' are in formula (X) as defined for formula (I) above. It is preferred that one or both acyl chains herein are modified to enable immobilisation to a solid substrate. It is in particular preferred to use a compound as represented by formula (XI):

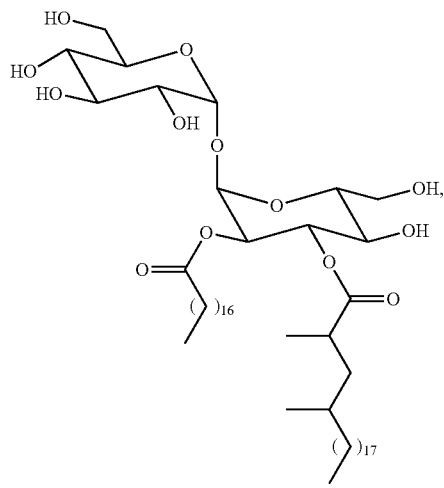

wherein one or both of the acyl chains are modified to enable immobilisation to a solid substrate. The acyl chains of the compound of formula (XI) may be substituted for any chain as defined in formula (IV), and the chains may be optionally modified to enable immobilisation to a solid substrate.

Suitable modification include the incorporation of a thio group on one of the acyl chains or the incorporation of a unsaturated bond at the end of one of the acyl chains, e.g. a double bond.

Suitable examples of such modified molecules include compounds according to formula (XII), which has an alkene group at the terminus of one of the acyl chains or (XIII) which has a thiol group at the terminus of one of the acyl chains.

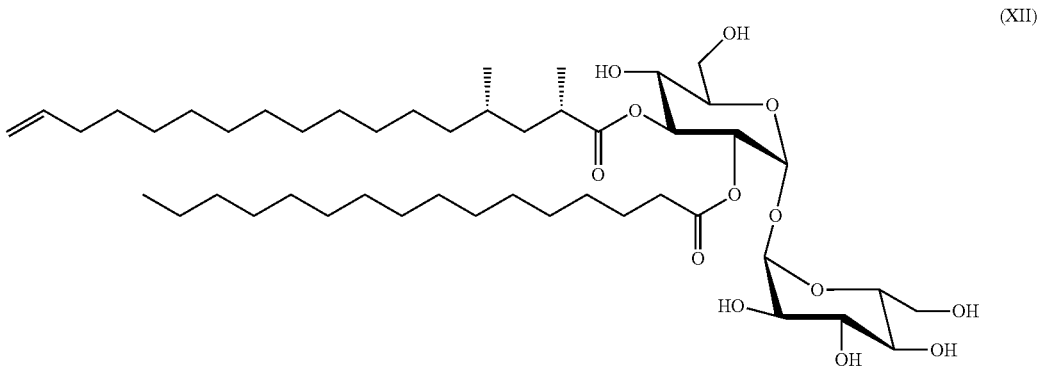

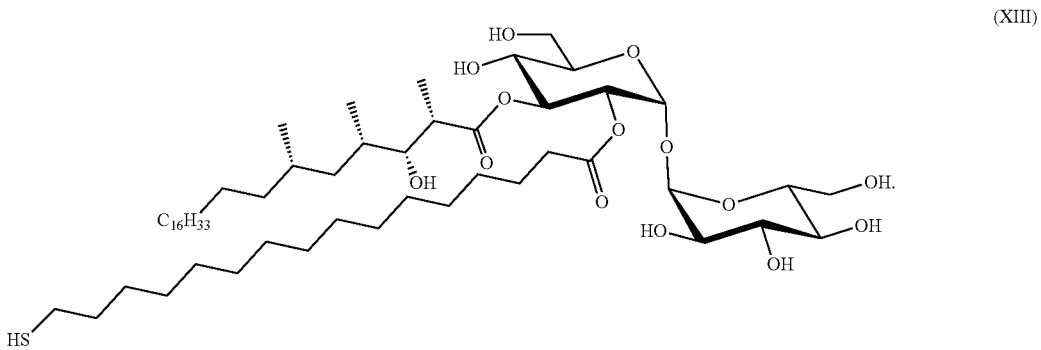

The alkyl chains of the compound of formulae (XII) and (XIII) may be substituted for any chain having the formula $C_nH_{n+1}$ or formula (IV) modified with the above shown alkene or thiol group.

The diacyl glycolipid antigens provide a means for obtaining high sensitivity of detection of markers for tuberculosis. Very high tuberculosis specific binding of antibodies to these antigens is detected in case of samples derived from patients that were tested smear negative. This makes it possible to diagnose TB in an early stage, in which there is a higher chance for successful treatment without complications compared to TB in a late stage. In addition, these particular antigens perform excellent when applied to samples derived from patients co-infected with HIV and tuberculosis.

The tuberculosinyl adenosine antigens as referred to in this application are compounds represented by the following formula (II),

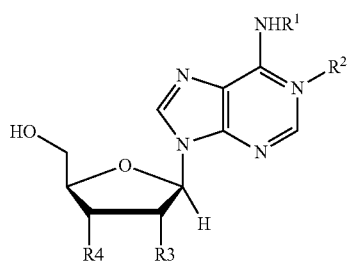

(II)

wherein in formula (II) $R^1$ is H or a group with formula (III)

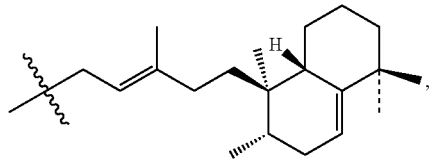

(III)

$R^2$ is absent or a group with formula (III), provided that one of $R^1$ and $R^2$ is a group with formula (III), $R^3$ and $R^4$ are selected independently from hydrogen, OH, an acyl chain, a carboxylic acid group comprising an acyl chain, in any combination thereof, wherein the antigens are optionally modified with one or more functional groups that enable immobilisation to a solid substrate, and enantiomers, diastereoisomers of the antigens, and mixtures thereof. In this formula it is preferred that $R^4$ is OH, and even more preferred that $R^4$ and $R^3$ are OH.

In formula (II) $R^1$ may be a group of formula (III) and $R^2$ may be absent. In other embodiments $R^1$ may be H and $R^2$ may be a group of formula (III). In case $R^2$ is a group of formula (III), the nitrogen to which it is attached carries a positive charge. The functional groups that enables immobilisation to a solid substrate is preferably included in the group of formula (III).

In case $R^3$ or $R^4$ are or comprise an acyl group it is preferred that only one of $R^3$ and $R^4$ is or comprises an acyl group, or in particular a fatty acid group. Acyl groups preferably have a suitable length and hydrophobicity to enable immobilisation to a solid substrate. The acyl chain may be modified with a functional group to enable immobilisation to a solid substrate. An acyl chain may be a mycolic acid chain as described in WO 2014/210327.

It is preferred that if the antigen of formula (II) has an acyl chain that the acyl chain is rather short. This makes the antigens more soluble in aqueous solutions and thus easier in use. The increased hydrophilicity that results from relatively short hydrocarbon chains makes the detection surface or sensor surface to which the antigens are immobilised more hydrophilic. Because of this, interactions of antibodies in the antigen occur easier and the speed of the detection will be enhanced. Moreover, it will be easier to synthesize the antigens in case synthetic antigens are used. In this respect in antigens with short acyl chains the acyl chain may be a linear or branched $C_1$-$C_{20}$ chain, such as a $C_5$-$C_{20}$ chain.

In a preferred embodiment the antigen of formula (II) is represented by a compound of formula (XIV) or (XV), optionally modified with one or more functional groups that enable immobilisation to a solid substrate.

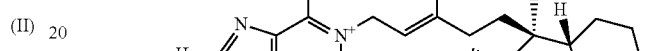
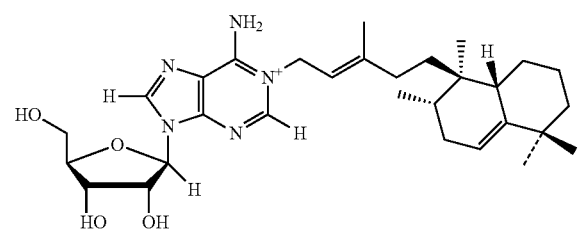

(XIV)

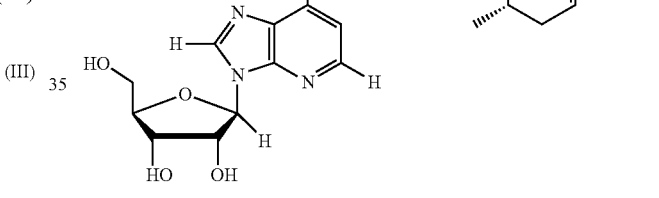

(XV)

It is preferred that the antigen in accordance with formula (II) is selected from the group of 1-tuberculosinyladenosine (as in formula (XIV)), 1-tuberculosinyl-2'-deoxyadenosine, 1-tuberculosinyl-O-acetyladenosine or a combination thereof. These compounds occur naturally in *Mycobacterium tuberculosis* bacteria and can be isolated therefrom. In this case the natural antigen may be used and, depending on the substrate to which it is to be immobilised, modified for immobilisation purposes if necessary. The levels of these compounds in Mycobacteria are rather low, much lower than for instance the levels of mycolic acid. Therefore, it is more advantageous to chemically synthesize these molecules, or to synthesize them in a production host micro-organism followed by isolation and optional further purification steps. This saves considerable costs. It is therefore preferred that these compounds are synthetic.

Synthetic antigens in accordance with formula (II) may for instance be synthetized in accordance with the method described in Buter et al., 2016.

The inventor has surprisingly found that if tuberculosinyl adenosine antigens as defined above are used in a method for detecting a marker for tuberculosis a very high tuberculosis specific binding of antibodies to these antigens is detected. The signal derived from the actual markers for tuberculosis is significantly less obscured by a background signal than when immobilised mycolic antigens are used, so that the signal derived from the actual markers for tuberculosis becomes more pronounced. This way the invention provides a significant improvement with regard to the sensitivity of detection of markers for tuberculosis. The inventor has further found that if tuberculosinyl adenosine antigens as defined above are used in a method for detecting a marker for tuberculosis in combination with other types of antigens that are capable of binding to an antibody which is indicative for the presence of mycobacterial material in a human or animal, a more reliable indication is provided that the subject from which the sample is derived has active tuberculosis. The inventor has observed in this respect that some other types of antigens such as the other antigens described herein, although they may serve as reliable markers of the presence of antibodies against mycobacterial material, may not distinguish between an active tuberculosis infection (such as in smear negative, smear positive, HIV-positive/tuberculosis co-infected, paediatric and extra-pulmonary patients) and an inactive tuberculosis infection (such as in a *Bacillus* Calmette-Guérin (BCG) vaccinated subject or a subject cured from a tuberculosis infection). The inventor has now discovered that antibodies against tuberculosinyl adenosine antigens as defined above are not properly detectable in samples derived from subjects vaccinated with a BCG vaccine or from subjects cured from a tuberculosis infection. In other words, if a sample contains a measurable amount of antibodies against tuberculosinyl adenosine antigens as defined above this is an indication of active tuberculosis. This makes it possible to distinguish in a tuberculosis test between subjects with active tuberculosis and subjects wherein the infection is inactive.

The antigens used in the invention may be isolated from *Mycobacterium tuberculosis* or be synthetic, i.e. obtained by full chemical synthesis or by synthesis in a production host which is not a *Mycobacterium*, for instance by transgenic expression, e.g. in *E. coli*, followed by isolation and optional further purification steps.

In the method of the invention method, one or more samples from a human or animal may be compared to a sample from a human or animal which is confirmed to be healthy and to a sample from a human or animal which is confirmed to have tuberculosis. For the sake of reliability it is highly preferred that all samples in one analysis undergo the same treatment in accordance with the steps of the method of the invention. The high specificity of at least the tuberculosinyl adenosine antigens and diacyl glycolipid antigens for tuberculosis specific antibodies and the associated lower risk of false positives make it even possible to reliably diagnose whether a person has tuberculosis without the necessity of a reference sample obtained from a healthy subject. The high specificity of at least the tuberculosinyl adenosine antigens and diacyl glycolipid antigens for tuberculosis specific antibodies and the associated lower risk of false positives also make it possible to reliably diagnose whether a person has tuberculosis without the necessity to divide a sample from a human or animal into two sample fractions of which one is exposed to antigens before the two fractions are exposed to a detection substrate with antigens such as for instance described in WO 2005/116654 or WO 2013/186679, where mycolic acids are used as the sole immobilised antigens. The method of the invention is therefore less difficult to perform and leads to fast and reliable diagnosis.

In the method of the invention a sample from a human or animal is provided. Normally the sample is derived from a human or animal which is suspected of having active tuberculosis, for instance a human or animal that had contact with someone suffering from tuberculosis or who resides in an area or travelled to an area with high prevalence of tuberculosis.

In order to be used in the methods of the invention samples may be used that have been collected at an earlier stage, stored until use under suitable conditions and provided at a suitable moment. Alternatively, a sample may be used in the detection method of the invention on the spot, i.e. as a point of care test.

The sample is preferably a blood derived sample. The sample may be a whole blood sample, a plasma sample or a serum sample. Blood serum is blood plasma without clotting factors and is preferred as plasma. The word plasma in this application may therefore as well refer to (blood) serum. Serum is preferred because it contains less different materials than blood plasma, which may lead to aspecific interactions or unwanted biological activity. In addition serum may have a lower viscosity than blood plasma. Using serum therefore may circumvent the need for diluting a sample, which saves time and materials.

In case the sample is a whole blood sample, the sample is preferably pre-filtered or separated to plasma or serum. A suitable filter for such a pre-filtering step is a 0.2 micron filter.

About 55% of whole blood consists of plasma/serum. If a whole blood sample is not filtered sufficiently or if the patient's physical situation necessitates it, it may be desired to dilute the whole blood sample or plasma or serum. The words plasma or serum in this application may therefore also refer to diluted plasma or serum. A dilution of the blood or plasma may therefore be implemented in the method of the invention, such as 5 to 10× dilution, a 10 to 20×dilution, a 20 to 50×dilution, a 50 to 100×dilution, a 250 to 5000× dilution, a 750 to 1250×dilution, such as for instance a 5×, 10×, 20×, 50×, 100×, 200×, 500×, 4000×, 2000× or 1000× dilution. Depending on the viscosity of the sample, such dilution may take place before the step of separating the plasma from the blood step (filter step or separating step). Alternatively dilution may take place after the filter step.

Dilution may be performed with any suitable diluent, for example a PBS based buffer, such as a blocking buffer. Such buffer may for example be a PBS/AE buffer comprising NaCl, KCl, $KH_2PO_4$, $Na_2HPO_4$ and EDTA in water at physiological pH. Such buffer may be a PBS based buffer consisting of 8.0 g NaCl, 0.2 g KCl, 0.2 g $KH_2PO_4$, and 1.05 g $Na_2HPO_4$ per liter of double distilled, deionized water containing 1 mM EDTA and 0.025% (m/v) sodium azide which is adjusted to pH 7.4.

The whole blood sample or plasma or serum may be further diluted with agents that prevent blood clotting, such as EDTA, heparine or citrate.

Optionally a detergent may be added in low concentration to the blood/plasma/serum to avoid sticking of components of the test system used.

For detection at least part of the sample is exposed to a solid substrate carrying the immobilised antigen, i.e. to a detection substrate, and binding of antibodies to the antigen is detected.

Possible combinations of antigens for use in the present invention are (mycolic acid derived antigens, tuberculosinyl adenosine antigens and diacyl glycolipid antigens are as defined above) combinations comprising or consisting of 2 or 3 types of antigens as follows:

1) Two Types of Antigens:

A) Tuberculosinyl adenosine antigens+mycolic acid derived antigens.

B) Diacyl glycolipid antigens+mycolic acid derived antigens.

C) Tuberculosinyl adenosine antigens+diacyl glycolipid antigens.

In case of a combination of two antigens combination C is preferred because the tuberculosinyl adenosine antigens perform particularly well in providing a reliable indication that the subject from which the sample is derived has active tuberculosis while the diacyl glycolipid antigens perform particularly well in case samples derived from smear negative persons are tested. This enables very sensitive detection of tuberculosis, irrespective of the bacterial load in a patient.

Moreover, the use of these antigens which each result in a specific output upon exposure to a sample from a subject suspected of having tuberculosis enables to provide information about the nature and/or disease state of the subject.

2) Three Types of Antigens

D) Diacyl glycolipid antigens+mycolic acid derived antigens+tuberculosinyl adenosine antigens.

In this embodiment, as an additional marker for the presence of antibodies mycolic acid derived antigens is used in combination with the diacyl glycolipid antigens and tuberculosinyl adenosine antigens. Although the use of mycolic acid involves a risk of false positive/negative signal, detection of binding of antibodies in the sample to mycolic acid derived antigens provides an additional indication of whether or not a person is infected with tuberculosis or not. This further enhances the reliability of the method of the invention. This combination of three antigens provides an excellent way of detecting tuberculosis and determining whether the tuberculosis is active or not.

In a preferred embodiment, except for the antigens mycolic acid derived type antigens, tuberculosinyl adenosine type antigens and diacyl glycolipid type antigens as defined in this application, no other types of antigens are used as immobilised antigens in the method, solid substrate and biosensor.

By using the above combinations tuberculosis can be detected in an early stage because of the high specificity for smear negative patients, and patients with active tuberculosis can be distinguished from a person with inactive tuberculosis infection, such as in a BCG vaccinated person or a person cured from a tuberculosis infection). Moreover, the use of multiple antigens which each result in a specific output upon exposure to a sample from a subject suspected of having tuberculosis enables to provide information about the nature and/or disease state of the subject.

In an exemplary embodiment in the combinations of A-D above, the tuberculosinyl adenosine antigen may be 1-tuberculosinyl adenosine, the mycolic acid derived antigen may be mycolic acid, and the diacyl glycolipid antigen may be the molecule according to formula (XIII), wherein the hydrophobic tails of these molecules may be modified for immobilisation.

In case a sample is exposed to multiple antigens binding of antibodies to the different types of antigens may be detected simultaneously, which is preferred. A sample may be divided in subsamples before exposure, each subsample dedicated to be exposed for a particular type of antigen. Simultaneous detection may be performed with one or more substrate carrying multiple types of antigens or with multiple substrates each carrying a particular type of antigen, for instance in a bioreactor comprising different compartments each containing a solid substrate with one type of antigen. The first type of antigens and one or more further type of antigens may be immobilised on a solid substrate. In this respect the invention also relates to a solid substrate which comprises a combination of immobilised antigens according to any of the combinations A-D above. In the method of the invention also different solid substrates may be used for performing one detection, each having a particular type of antigen immobilised thereto.

In this respect, it is preferred that at least part of the sample is exposed to the solid substrate with the immobilised antigen or multiple types of immobilised antigens as described above; followed by detecting binding of antibodies to the antigens immobilised to said substrate.

Binding of the antibodies to the immobilised antigens can be detected by means of any assay that involves measurement of change of mass on the substrate, change of refractive index, change of entropy, change of enthalpy, viscosity change, temperature change, colour change etc.

Detection of binding of antibodies to the antigen on the detection substrate may take place with any suitable detection method, including simple visual detection or methods that include voltametrical, amperometrical or any electrochemical detection.

Detection of binding of antibodies to the antigen on the detection substrate may take place in real time or by means of an end-point assay.

In a real time method, because detection takes place in real time, binding of antibodies to the antigens immobilised on the detection substrates is directly detected during the binding process. For detection in principle all real-time, label free analysis techniques may be used.

Suitable real time detection assays include surface plasmon resonance or electrochemical impedance spectroscopy, isothermal titration calorimetry, bio-layer interferometry, optical gratings, photonic crystal, acoustic resonant profiling, quartz crystal microbalances.

In a real time detection method, the solid substrate carrying the antigen may be silica based, such as substrates based on silicium dioxide. In such an embodiment the antigens are preferably modified at one or both of the acyl chains with a functional group that enables immobilisation. Silica based substrates are particularly useful when ring resonance technology is used to detect binding of antibodies to the immobilised antigens. Preferably the detection is carried out using a biosensor chip using a Si-based ring resonator. This enables the method of the invention to be carried out with a very compact device.

It is also well possible that the solid substrate is gold based. Gold based substrates are particularly useful when surface plasmon resonance or electrochemical impedance spectroscopy are used to detect binding of antibodies to the immobilised antigens.

The detection of binding of antibodies and/or other material to the antigen on the detection substrate may be carried out in an automated device. Various automated devices will be known to the person skilled in the art and the skilled person will be able to select suitable software means to determine the degree or extent of binding to the detection substrate.

Detection of binding of antibodies to the antigen on the detection substrate may also take place by means of an end-point assay. The term "end-point assay" is to be understood as an assay wherein the outcome of interest is the end result after a fixed assay incubation period, in contrast to the aforementioned real-time assay. An end-point detection assay may for instance detect changes to levels of color, fluorescence, absorbance or luminescence at the end of a test.

Suitable end-point assays include enzyme-linked immunosorbent assay (ELISA), Western blotting, radioactive labelling assay, photospectrometric assay, immunofluorescence, immunoprecipitation, immunocytochemistry, immunohistochemistry, amperometric or voltametric detection assays, or electrochemical impedance spectroscopy.

In a preferred embodiment of an end-point assay detection takes place by means of an immunogold filtration assay. In such an assay the detection substrate is a microporous membrane, preferably a nitrocellulose membrane or a PVDF membrane, to which an antigen is immobilised.

In an end-point assay interaction of antibodies with the antigens may be carried out using secondary antibodies that bind the heavy chain of the primary antibodies that bind to the immobilised antigens. Many suitable secondary antibodies are commercially available. The secondary antibody may be coupled to nanoparticles or beads, for instance gold beads, or associated with liposomes. Examples of secondary antibodies may be protein A or G, possibly conjugated with an enzyme that enables detection.

A particular suitable technique or detecting the binding of antibodies to the immobilised antigens on the detection substrate is the so-called immunogold filtration assay (IGFA), and in particular the dot immunogold filtration assay (DIGFA).

Immunogold filtration assays are methods combining ELISA and immunogold technique and are methods in which a sample to be assayed is allowed to filtrate through a microporous membrane, preferably a nitrocellulose membrane, and is captured by a capture probe coated on the membrane. A colloidal gold-labelled probe is allowed to filtrate through the microporous membrane in the same manner. By using a microporous membrane as the carrier for the capture probe and employing the capillary action and permeability of the membrane, antigens and antibodies can easily react and may conveniently be subjected to optional washing and/or blocking steps. When the colloidal gold-labelled probe binds to the capture probe the colloidal gold particles aggregate and a red dot appears which is visible with the naked eye.

In case the end-point assay of the present invention is an immunogold filtration assay, the antigen is immobilised on a microporous membrane, preferably a nitrocellulose membrane. After immobilising the antigen onto the microporous membrane, the optionally pre-treated samples can be applied to the membrane. After addition of the sample fractions and reaction of the immobilised antigens with the antibodies contained in the samples on the membrane, colloidal gold-labelled second antibodies can be added onto the membrane to have gold particle aggregation in the antigen-antibody reaction place. In case of aggregation visible red or brown spots are formed. The intensity of the spot is proportional to the amount of reactions between antigen and antibody, i.e. to the amount of antibodies in the sample. In other words a sample from a person suffering from tuberculosis will result in a more intense spot than a sample from a person which is healthy.

Immunogold filtration assays are simple and rapid detection methods because no instruments are required except a membrane and the reagents and the results can be observed by the naked eye within a few minutes.

In an immunogold filtration assay the microporous membrane may be for example a nitrocellulose membrane, a cellulose acetate membrane or a PVDF membrane with a suitable pore diameter. Preferably, nitrocellulose is used. A suitable pore diameter is 0.2 to 5 µm.

Between the various steps of an immunogold filtration assay the membrane may be washed with a suitable buffer, for example a PBS based buffer. Such buffer may for example be a PBS/AE buffer comprising NaCl, KCl, $KH_2PO_4$, $Na_2HPO_4$ and EDTA in water at physiological pH. Such buffer may be a PBS based buffer consisting of 8.0 g NaCl, 0.2 g KCl, 0.2 g $KH_2PO_4$, and 1.05 g $Na_2HPO_4$ per liter of double distilled, deionized water containing 1 mM EDTA and 0.025% (m/v) sodium azide which is adjusted to pH 7.4.

In case DIGFA is used, the antigen may be immobilised to the microporous membrane in a dot wise manner. In a DIGFA assay the samples are also applied to the membrane in the form of dots. Also the colloidal gold-labelled second antibodies are added in the form of dots. A DIGFA assay is particularly preferred because at different spots on several membranes various antigens deriving from various mycobacterial strains may be immobilised. This way it becomes possible to provide information on which mycobacterial strain a patient is infected with. Another advantage of using DIGFA is that samples derived from different persons can be compared in one test, because DIGFA enables fast and reliable detection of antibody-antigen interaction in an unlimited amount of spots, depending on the size of the membrane.

The detection of binding of antibodies and/or other material to the immobilised antigens, for instance the red staining in case a DIGFA assay is used as a detection method, may be carried out in an automated device. Various automated devices will be known to the person skilled in the art and the skilled person will be able to select suitable software means to quantify the degree or extent of binding on the detection substrates.

The detection of binding of antibodies and/or other material to the immobilised antigen may be performed by a visual detection technique or any other suitable detection technique. In a particular preferred embodiment, detection by means of the end-point assay takes place visually, preferably with the naked eye. This has the advantage of easy detection without the need for expensive and complicated detection technology. In case DIGFA is used, binding of antibody antibodies and/or other material to the immobilised antigens may be assessed by means of the naked eye.

A visual signal, e.g. the red staining in case a DIGFA assay is applied as end-point assay, may also be detected with help of a mobile app, i.e. a computer program designed to run on mobile devices such as tablet computers or smart phones. For instance, an app can be used that is designed to compare the binding signal between different samples or sample fractions and which indicates whether the human or animal from which the sample originated has tuberculosis.

The method of the invention may comprise additional steps that are advantageous for the sensitivity of the method. For instance the method may contain further steps of exposing the sample to molecules that have affinity for molecules in the sample that lead to a binding signal which is not specific for tuberculosis in order to scavenge away these non-specific molecules.

The method may also contain further steps of dividing the sample. As mentioned above, the high specificity of in particular the diacyl glycolipid antigens and the tuberculosinyl adenosine for tuberculosis specific antibodies and the associated lower risk of false positives also make it possible to reliably diagnose whether a person has tuberculosis without the necessity to divide a sample from a human or animal into two sample fractions of which one is exposed to antigens before the two fractions are exposed to a detection substrate with antigens. Nevertheless, the antigens mentioned herein would be suitable in such a method.

In one embodiment the method of the invention therefore may be a real-time method comprising the steps of:
  i) providing a sample from a human or animal;
  ii) obtaining at least two fractions of said sample;
  iii) exposing the first of said fractions to a solid substrate carrying immobilised antigens,
  iv) exposing the second of said fractions to a solid substrate not carrying immobilised antigens;
  v) exposing the sample fraction exposed in step iii) to a solid test substrate which is a solid substrate as described above for the first aspect of the invention and exposing the sample fraction exposed in step iv) to a solid control substrate which has the same composition as the solid test substrate;
  vi) detecting binding of antibodies to the immobilised antigens of step v) in real time; and
  vii) comparing the degree or extent of binding between the test and control substrates, any observed lesser binding to the test substrate being an indicator of the presence of antibodies to the immobilised antigen in the sample that indicates tuberculosis in the human or animal from which the samples originated, wherein the antigens immobilised to the solid substrate of step iii) comprise at least one type, preferably all the types of antigens that are immobilised to the solid test and control substrates.

In a comparable embodiment, the method of the invention may be an end-point method of detecting antibodies against mycobacterial material in a sample, comprising the steps of:
  i) providing a sample from a human or animal;
  ii) obtaining at least two fractions of said sample;

iii) exposing the first of said fractions to a solid substrate carrying immobilised antigens;

iv) exposing the second of said fractions to a solid substrate not carrying immobilised antigens; or storing at least part of the second of said fractions until step v), skipping the step of exposing the second of said fractions to a solid substrate not carrying immobilised antigens;

v) exposing at least part of the sample fraction exposed in step iii) to a solid test substrate which is a substrate which is a solid substrate as described above for the first aspect of the invention and exposing the sample fraction exposed or stored in step iv) to a solid control substrate which has the same composition as the solid test substrate;

vi) detecting binding of antibodies to the immobilised antigen of step v) in an end-point assay; and vii) comparing the degree or extent of binding between the test and control substrates, any observed lesser binding to the test substrate being an indicator of the presence of antibodies to the immobilised antigen in the sample that indicates tuberculosis in the human or animal from which the samples originated, wherein the antigens immobilised to the solid substrate of step iii) comprise at least one type, preferably all the types of antigens that are immobilised to the solid test and control substrates.

In the context of these embodiments it should be understood that lesser can be interpreted qualitatively and quantitatively, i.e. lesser binding may be interpreted as having less binding events as well as having weaker bindings. The advantage of these two embodiments is that no sample of a healthy person is required as a reference or control sample, even if there is still background signal. Only one sample from one subject is necessary.

Further, the substrate to which the antibody is immobilised in step iii) of these embodiments is in general not made of the same material as the test/control substrate. The substrate in step iii) may be made of any material that is inert for non-specific binding of molecules of the sample. Such materials include polytetrafluorethylene (e.g. Teflon®), polypropylene, polyetherketone (PEEK) and polyethylene. The test and control substrates in these embodiments are sensing surfaces or substrates of a detection device or detection surfaces or substrates in a detection assay as discussed above.

To the solid substrate of the invention, together with the antigens, compounds may be immobilised to control the hydrophobicity/hydrophilicity of the solid substrate. In particular when antigens are immobilised that have long acyl chains the substrate's surface may become too hydrophobic for efficient binding of antibodies. In that case it may be preferred to immobilise the antigens to the solid substrate in a less dense packing. This may be obtained by co-immobilisation of hydrophilic molecules distributed between the antigens or by immobilization of the antigens onto hydrophylic molecules that are immobilized to the solid substrate. Such hydrophilic molecules may for instance be PEG or mPEG.

The solid substrate may contain any combination of antigens that are capable of binding to antibodies which are indicative for tuberculosis, but at least one of the combinations A-D as specified above.

The antigens may be co-immobilised to the same solid substrate or be provided on separate solid substrates. The latter enables detection of binding of antibodies to the different types of antigens on separate sections or in separate compartments of a biosensor or in sequence.

Examples of solid substrates may thus comprise:
two types of antigens capable of binding to an antibody which is indicative for the presence of mycobacterial material in a human or animal, such as a solid substrate with 1-tuberculosinyladenosine antigens antigens and $Ac_2SGL$ antigens immobilised thereto; a solid substrate with 1-tuberculosinyladenosine antigens and mycolic acid antigens immobilised thereto; or a solid substrate with $Ac_2SGL$ antigens and mycolic acid antigens immobilised thereto;

a solid substrate with three types of antigens capable of binding to an antibody which is indicative for the presence of mycobacterial material in a human or animal, such as a solid substrate with 1-tuberculosinyladenosine antigens, $Ac_2SGL$ antigens and mycolic acid antigens immobilised thereto. In the method of the invention also different solid substrates may be used for performing one detection assay, each having a particular type of antigen immobilised thereto in any of the combinations mentioned above.

The way antigens are immobilised to a substrate depends on the characteristics of the substrate to which the antigens are immobilised.

Some substrates allow immobilisation of antigens without modification, for instance by means of hydrophobic interaction of one or both of the hydrophobic carbon chains, such as acyl chains, of the antigen with the substrate. This would for instance be possible if the antigens are immobilised to the surface of an ELISA plate, a nitrocellulose membrane or a PVDF membrane. For these substrates, the most convenient immobilisation method is direct physical absorption of the antigen to the assay membrane.

Other substrates may require modification of the antigen with a functional group. The term "functional group" in this application is therefore to be understood as a group that enables immobilisation of the antigen to a solid substrate. These functional groups are preferably added to one or both of the hydrophobic carbon chains of the antigens.

Regarding the tuberculosinyl adenosine antigens, functional groups may be added to one or more of the hydrophobic carbon chains of the antigens, e.g. the alkyl chains. Alternatively, functional groups may be added to the nitrogen or amine of the adenosine moiety. Alternatively, functional groups may be added to the tuberculosinyl tail with formula (III) of the antigen. Regarding the diacyl glycolipid antigens, the functional groups are preferably added to one or both of the hydrophobic carbon chains of the antigens, i.e. the acyl chains of the diacyl glycolipid antigens. Such a functional group can for instance be a thio group, an amine group, an aldehyde group or any other suitable group.

Such a functional group can for instance be a thio group, an amine group, an aldehyde group, a double bond (i.e. an alkene group) or any other suitable group.

Some coupling methods require that apart from the antigen also the solid substrate to which the antigens are coupled is modified. Examples of modified substrates include:

NHS ester-activated support materials, wherein NHS esters are reactive groups formed by EDC activation of carboxylate molecules to react with primary amines on the antigen;

Aldehyde-activated support materials, wherein coupling of the antigen takes place by a reaction called reductive amination;

Azlactone-activated support materials, involving co-polymerization of acrylamide with azlactone;

CDI-activated support materials, wherein carbonyl diimidazole (CDI) activates hydroxyls to form reactive imidazole carbamates that form carbamate linkages with primary amine-containing/modified antigens;

Sulfhydryl-reactive support materials, wherein the thiol group can be used for direct coupling reactions;

Maleimide-activated support materials, wherein maleimide-activated reagents form stable thioether linkages;

Iodoacetyl-activated support materials, which react with sulfhydryl groups resulting in stable thioether linkages;

Pyridyl disulfide support materials, wherein pyridyl disulfides react with sulfhydryl groups; and Hydrazide-activated support materials.

Antigens can be immobilised or "coupled" directly to solid support material by formation of covalent chemical bonds between particular functional groups on the (modified) antigen (e.g., primary amines, sulfhydryls, carboxylic acids, aldehydes) and reactive groups on the support material. It is also possible that antigens are immobilised non-covalent binding such as hydrophobic interaction or via streptavidin-biotin coupling. Various coupling methods are possible. For instance, thio coupling, amine coupling and carbonyl-reactive immobilisation methods, which involve coupling through carbonyl (sugar) groups where cis-diols can be oxidized with sodium periodate to create aldehydes as sites for covalent immobilisation. Also self-assembly immobilisation methods are possible. For instance, a silica based substrate may be modified with a silane derivative containing a free amine group, e.g. aminopropyltriethoxysilane or aminomethoxysilane. This free amine group reacts spontaneously with a thiol modified antigen to form a covalent bond. This does not require complicated protocols. In case of a gold solid substrate, a thiol cysteamine monolayer may be applied to the gold substrate, the free amine of the thiol cysteamine may than be applied in a spontaneous coupling reaction with a thiol modified antigen. This would not require complicated protocols. Regarding coupling to nitrocellulose membranes, coupling may be based on various mechanisms. An unmodified antigen may be immobilised to the membrane with its hydrophobic tail(s) as discussed above, but other mechanisms are also possible. Such mechanisms include covalent attachment of thiolated antigen to an epoxide-functionalized nitrocellulose membrane, attachment of a biotinylated antigen through a nitrocellulose-binding streptavidin anchor protein, and fusion of an antigen to a novel nitrocellulose-binding anchor protein for direct coupling and covalent attachment through an epoxide thiol linkage using a functionalized nitrocellulose membrane immobilisation.

For purposes of detection of the presence of antibodies in a sample the antigens are immobilised to a solid substrate which can be exposed to a sample derived from a human or animal so that binding of antibodies to the immobilised antigens can be determined, either qualitatively or quantitatively or both. It is noted that in this application the term "solid substrate" means the same as "solid surface" or "solid support".

The solid substrate may be a sensing surface or substrate of a detection device or a detection surface or substrate in a detection assay. In this respect, the substrate to which the antigens are immobilised may be a sensing surface of a surface plasmon resonance device, electrochemical impedance spectroscopy device, isothermal titration calorimetry device, bio-layer interferometry device, optical gratings device, photonic crystal device, acoustic resonant profiling device, or quartz crystal microbalance device or a detection surface in an enzyme-linked immunosorbent assay (ELISA), a Western blotting assay, radioactive labelling assay, photo-spectrometric assay, immunofluorescence, immunoprecipitation assay, immunocytochemistry assay, immunohistochemistry assay, voltametric detection assay, amperometric detection assay or electrochemical impedance spectroscopy assay.

The immobilised solid substrate of the invention can be used in a biosensor. This biosensor comprises a combination of 2 or more of the tuberculosinyl adenosine antigens, diacyl glycolipid antigens, and mycolic acid derived antigens as defined above immobilised to one or more solid substrates. The antigens may be immobilised to one and the same substrate mixed or at separate locations or at different substrates in the biosensor. Using separate locations or separate substrates enables analysis of the nature of a possible tuberculosis infection for instance for obtaining an indication whether the tested person has active tuberculosis. In one embodiment therefore multiple types of antigens are immobilized to the same substrate. In another embodiment of the biosensor, each type of antigen is immobilized on a separate substrate.

The combination of antigens in the biosensor may be any of the combinations A-D as described above.

The biosensor can be any biosensor which is suitable for use in the method according to the invention. For instance, the biosensor may comprise a silica based substrate with immobilised antigens and a Si ring resonator. Such a biosensor can be used for ring resonance. It is also well possible that the substrates of the chambers of the biosensor are gold based. Gold based substrates are particularly useful when surface plasmon resonance or electrochemical impedance spectroscopy are used to detect binding of antibodies to the immobilised antigens. The invention also encompasses any other biosensor comprising the solid substrate of the invention.

EXAMPLES

The following examples are meant to illustrate the principle of the invention and should not be interpreted as limiting the scope of the claims. In the example human serum samples were tested for antibodies that are specific for the presence of mycobacterial material in a human or animal in an ELISA assay. As a detection method an ELISA method was chosen because it is less sensitive than for example Surface Plasmon Resonance or electrochemical impedance spectroscopy (EIS) or Ring Resonance (Interferometry). Therefore it can be concluded that if satisfactory results are obtained with ELISA, these will also be obtained with more sensitive detection methods.

Materials:
Sample (human plasma or serum)
0.2 micron spinfilters (Whatman)
polyclonal mycolic acid dissolved in hexane,
synthetic $Ac_2SGL$ (2-palmitoyl-3-hydroxyphthio-ceranoyl-2'-sulfate-$\alpha$-$\alpha$'-D-trehalose) dissolved in hexane,
synthetic 1-tuberculosinyladenosine (TbAd) dissolved in hexane,
synthetic diacyl glycolipid antigen in accordance with formula (XIII)
Polystyrene ELISA plates
PBS
Blocking buffer: 0.5% casein in PBS
1-step ultra TMB-ELISA substrate solution (Thermo Scientific)
2M sulfuric acid
Secondary antibody: rabbit anti-human IgG HRP or rabbit anti-human IgM HRP (DAKO)
Procedures
Coating of ELISA Plates
To immobilise mycolic acid to ELISA plates to each well 50 μl of hexane with polyclonal mycolic acid in a concentration 100 μg/ml per well of 96-wells ELISA plate was added. To immobilise $Ac_2SGL$ to ELISA plates to each well of 96-wells ELISA plates 50 μl (of hexane with $Ac_2SGL$ in a concentration of 100 μg/ml was added. To immobilise 1-tuberculosinyladenosine to ELISA plates to each well of 96-wells ELISA plates 50 μl (of hexane with 1-tuberculosinyladenosine in a concentration of 100 μg/ml was added. Plates were incubated for 24 hrs at 4° C. and subsequently washed two times with PBS. To immobilise 1-tuberculosinyladenosine to ELISA plates to each well of 96-wells ELISA plates Immobilised diacyl glycolipid antigen in accordance with formula (XIII) was immobilised via the terminal thio group. 1 μg of antigen according to formula (XIII) was immobilised per well.
Sample Preparation
Serum derived from humans that were known to be suffering of tuberculosis was derived from both smear positive (Patients 1-9 (+)) and smear negative patients (Patients 11-18 (−)). Samples of patients 19-40 tested for anti-TbAd antibodies are a random selection of smear negative and positive patients. Also samples were used derived from healthy humans (Healthy 1, 2 and 3). Fractions of 0.5 ml were obtained and transferred each to a 0.2 micron spin filter and centrifuged at 10000 g. The flow-through was diluted 1:20 in blocking buffer.

ELISA-Procedure

To block aspecific binding of antibodies with the antigens in the wells of the ELISA plates, 300 µl of blocking buffer was added to each well and incubated for 1 hour. Subsequently, the blocking buffer was replaced with 45 µl of sample. Blocking buffer was used as a negative control. After incubation, the plates were washed three times with PBS. The washing PBS buffer was replaced with HRP-conjugated secondary antibody in blocking buffer (1:20.000 diluted). After incubation, the plate was washed again three times with PBS. Subsequently 50 µl per well of TMB-ELISA substrate solution was added to the wells and incubated for 15-30 min at room temperature. The reaction was stopped by adding 50 µl per well of 2 M sulphuric acid. Absorbance at 450 nm was measured to quantify the binding of antibodies to the immobilised antigens of the ELISA plate.

Results

FIG. 1 shows the results of an ELISA test with rabbit anti-human IgM HRP as secondary antibody using immobilised mycolic acid. It is clear that very high background signal is obtained in the healthy persons (healthy 1 and 2, white bars). As these persons were confirmed to be healthy and samples from these persons thus do not contain antibodies against mycobacterial material, this signal is the result of materials that are unrelated to tuberculosis that do bind to mycolic acid and lead to an ELISA signal. The samples derived from smear negative patients (patients 11-18 (−), grey bars) show absorbance signals which do not significantly exceed the signal of the healthy persons. The samples derived from smear positive patients (patients 1-9 (+), black bars) show absorbance signals which even seem lower than the signal of the healthy persons. The high background signal derived from materials that are unrelated to tuberculosis but that do bind to mycolic acid thus obscures the signal derived from the actual antibodies that indicate tuberculosis.

Figure 2:
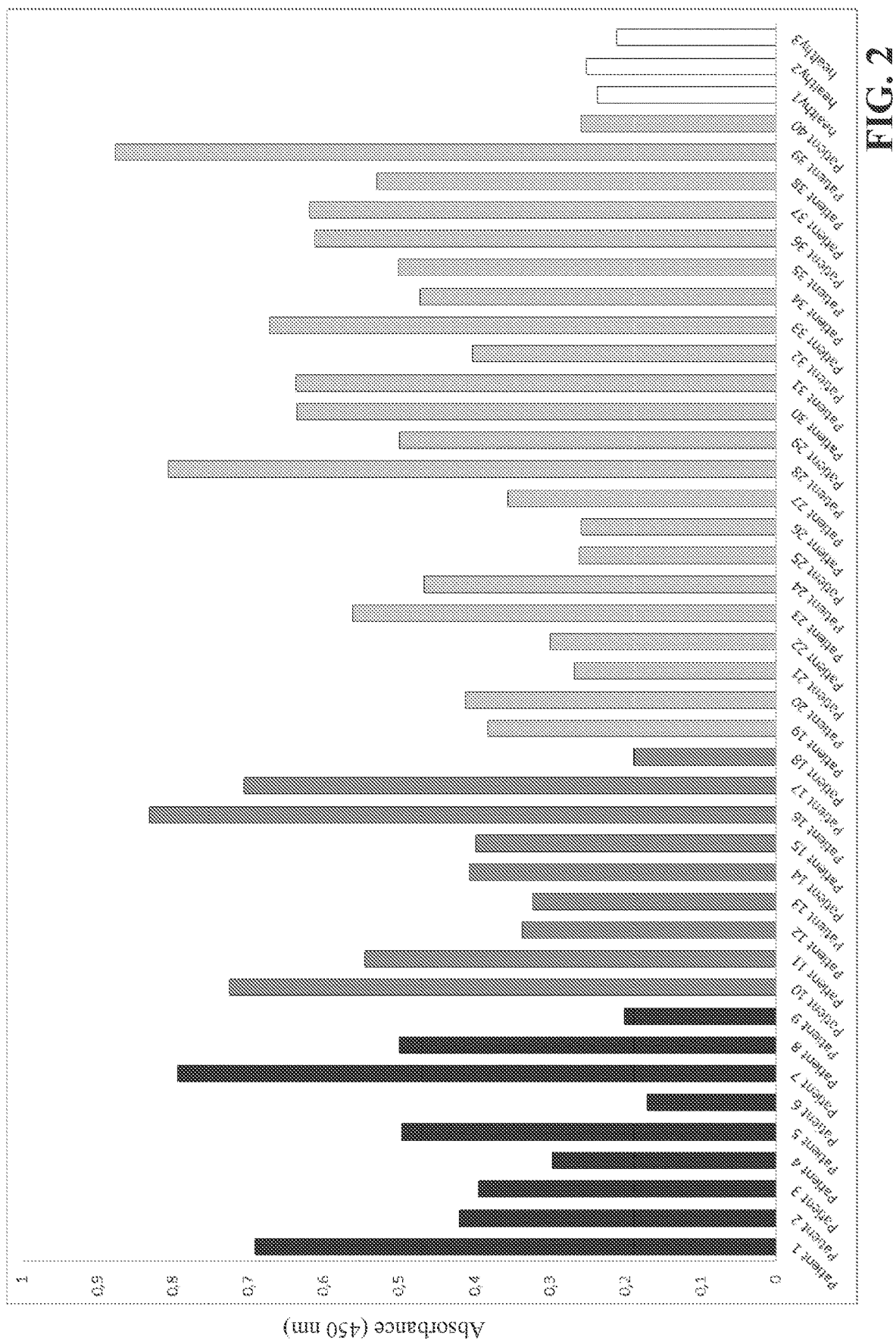
FIG. 2 shows a diagram of ELISA results using tuberculosinyl adenosine antigens immobilised on ELISA plates (IgM as secondary antibody).

FIG. 2 shows ELISA tests with rabbit anti-human IgM HRP as secondary antibody that were performed with immobilised 1-tuberculosinyladenosine. Here the background signal obtained in the healthy persons (healthy 1, 2 and 3 white bars) appears to be markedly lower than that is obtained by using mycolic acids as immobilised antigens. The results in FIG. 2 show that if these immobilised antigens are used in a method for detecting a marker for tuberculosis a very high tuberculosis specific binding of antibodies to these antigens is detected, regardless of whether the samples are derived from smear positive (patients 1-9 (+), black bars) or smear negative persons (patients 10-18 (−), dark grey bars) as the signals of both are similar the signals of the random samples (19-40). This high specificity is clearly not the case when mycolic acids immobilised to a solid substrate are applied. The signal derived from antibodies against 1-tuberculosinyladenosine appears to be significantly less obscured by a background signal than when immobilised mycolic antigens are used. This results in a significant improvement with regard to the sensitivity of detection of markers for tuberculosis.

Figure 3:
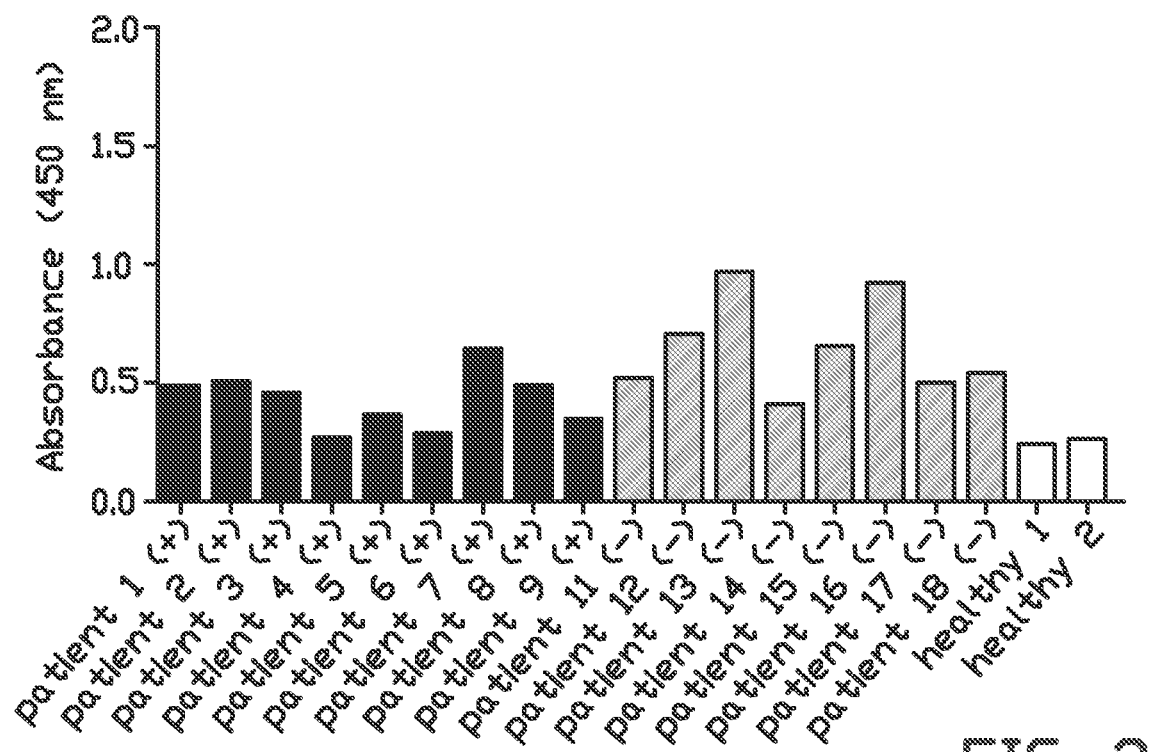
FIG. 3 shows a diagram of ELISA results using diacyl glycolipid antigens immobilised on ELISA plates (IgM as secondary antibody)

FIG. 3 shows that when ELISA tests with rabbit anti-human IgM HRP as secondary antibody were performed with immobilised Ac$_2$SGL, the background signal obtained in the healthy persons (healthy 1 and 2, white bars) appears to be markedly lower. The samples derived from smear positive patients (patients 1-9 (+), black bars) show absorbance signals which are higher than the signal of the healthy persons, thus confirming the presence of specific antibodies that indicate tuberculosis. This effect is even more pronounced in the samples derived from smear negative patients (patients 11-18 (−), grey bars) which show absorbance signals which are significantly higher than the signal of the healthy persons. The results in FIG. 3 show that if these immobilised antigens are used in a method for detecting a marker for tuberculosis a very high tuberculosis specific binding of antibodies to these antigens is detected. This effect is most pronounced in samples that are derived from patients that were tested smear negative. The signal derived from the actual markers for tuberculosis appears to be significantly less obscured by a background signal than when immobilised mycolic antigens are used, so that the signal derived from the actual markers for tuberculosis becomes more pronounced. This results in a significant improvement with regard to the sensitivity of detection of markers for tuberculosis.

Figure 4:
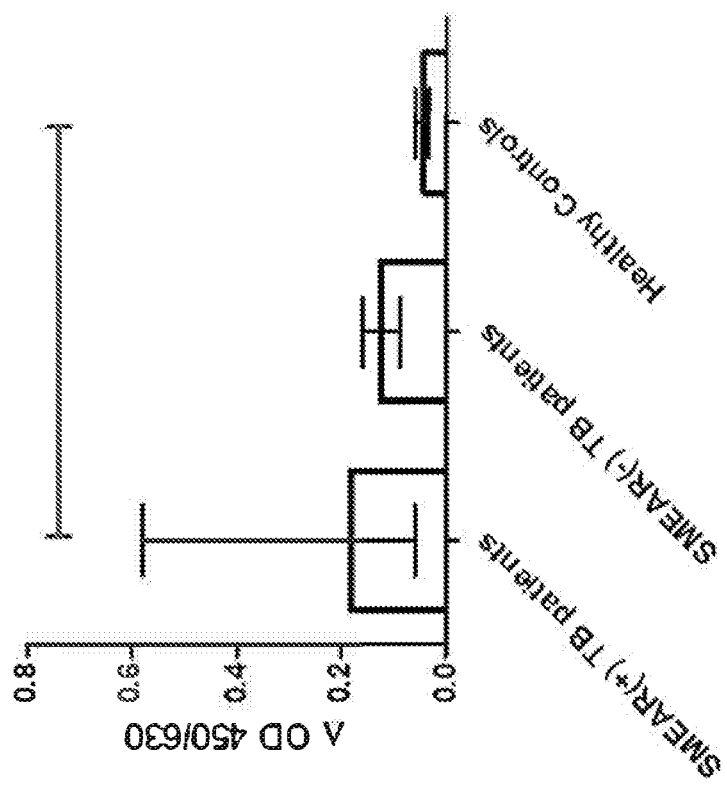
FIG. 4 shows a diagram of ELISA results using diacyl glycolipid antigens according to formula (XIII) immobilised on ELISA plates.

FIG. 4 shows that when ELISA tests were performed with an immobilised diacyl glycolipid antigen in accordance with formula (XIII), the background signal obtained in the healthy persons (n=4) appears to be markedly lower. The samples derived from smear positive patients (n=9) show absorbance signals which are higher than the signal of the healthy persons, albeit with a rather high standard deviation, thus confirming the presence of specific antibodies that indicate tuberculosis. This effect is even more pronounced in the samples derived from smear negative patients (n=32) which show absorbance signals which are significantly higher than the signal of the healthy persons, and which signals show very low standard deviation. The above results show that if the immobilised antigens in accordance with formula (XIII) are used in a method for detecting a marker for tuberculosis a very high tuberculosis specific binding of antibodies to these antigens is detected. This effect is most significant, because of the low standard deviations, in samples that are derived from patients that were tested smear negative. The signal derived from the actual markers for tuberculosis appears to be significantly less obscured by a background signal than when immobilised mycolic antigens are used, so that the signal derived from the actual markers for tuberculosis becomes more pronounced. This results in a significant improvement with regard to the sensitivity of detection of markers for tuberculosis.

REFERENCES

WO 2005/116654
WO 2013/186679
WO 2014/210327
EP 1 950 218 A1
Buter J, Heijnen D, Wan I C, Bickelhaupt F M, Young D C, Otten E, Moody D B, Minnaard A J. J Org Chem. 2016 Jul. 11.
van Summeren, R. P., Moody, D. B., Feringa, B. L., Minnaard, A. J., Summeren, R. P. V. & Feringa, B. 12 Apr. 2006 In: Journal of the American Chemical Society
D. Geerdink, B. ter Horst, M. Lepore, L. Mori, G. Puzo, A. K. H. Hirsch, M. Gilleron, G. de Libero and A. J. Minnaard, Chem. Sci., 2013, p. 709-716

The invention claimed is:

1. A method of diagnosing active tuberculosis in smear negative patients, comprising detecting the presence of antibodies against mycobacterial material in a sample comprising the steps of: providing a sample from a human or animal; and detecting binding of antibodies in said sample to a 2-palmitoyl-3-hydroxyphthioceranoyl-2'-sulfate-α-α'-D-trehalose antigen.

2. The method according to claim 1, wherein the antigen is immobilised to one or more solid substrates.

3. The method according to claim 2, wherein detecting the binding of the antibodies to the immobilised antigen involves measurement of change of mass on the substrate, change of refractive index, change of entropy, change of enthalpy, viscosity change, temperature change, or colour change.

4. The method according to claim 2, wherein detecting of binding of antibodies to the immobilised antigen takes place by an end-point assay.

5. The method according to claim 4, wherein the end-point assay is selected from the group consisting of enzyme-linked immunosorbent assay (ELISA), Western blotting, radioactive labelling assay, photospectrometric assay, immunofluorescence, immunoprecipitation, immunocytochemistry, immunohistochemistry, and electrochemical impedance spectroscopy.

6. The method according to claim 1, wherein said smear negative patients comprise extra-pulmonary tuberculosis patients, pediatric tuberculosis patient or patients co-infected with HIV and tuberculosis.

7. The method according to claim 1, wherein detection is carried out using surface plasmon resonance, electrochemical impedance spectroscopy, isothermal titration calorimetry, bio-layer interferometry, optical gratings, photonic crystal, acoustic resonant profiling or quartz crystal microbalances.

* * * * *